United States Patent
Uemori

(10) Patent No.: US 10,342,418 B2
(45) Date of Patent: *Jul. 9, 2019

(54) IMAGE PROCESSING DEVICE AND IMAGE PROCESSING METHOD

(71) Applicant: Sony Corporation, Tokyo (JP)

(72) Inventor: Takeshi Uemori, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/246,145

(22) Filed: Aug. 24, 2016

(65) Prior Publication Data

US 2016/0364870 A1    Dec. 15, 2016

Related U.S. Application Data

(63) Continuation of application No. 14/625,052, filed on Feb. 18, 2015, now Pat. No. 9,456,732.

(30) Foreign Application Priority Data

Feb. 24, 2014    (JP) ................. 2014-032809

(51) Int. Cl.
| | | |
|---|---|---|
| *G06K 9/00* | (2006.01) |
| *A61B 1/04* | (2006.01) |
| *A61B 1/00* | (2006.01) |
| *G06T 7/00* | (2017.01) |
| *A61B 1/06* | (2006.01) |
| *G06T 7/73* | (2017.01) |
| *G06T 7/254* | (2017.01) |

(52) U.S. Cl.
CPC ............ *A61B 1/04* (2013.01); *A61B 1/00009* (2013.01); *A61B 1/00057* (2013.01); *A61B 1/00193* (2013.01); *A61B 1/06* (2013.01); *G06T 7/0002* (2013.01); *G06T 7/0012* (2013.01); *G06T 7/254* (2017.01); *G06T 7/74* (2017.01); *G06T 2207/10016* (2013.01); *G06T 2207/10068* (2013.01); *G06T 2207/30004* (2013.01); *G06T 2207/30168* (2013.01)

(58) Field of Classification Search
CPC ........................................................ A61B 1/06
See application file for complete search history.

(56) References Cited

U.S. PATENT DOCUMENTS

2007/0088193 A1*  4/2007  Omori ................ A61B 1/00059
                                                                      600/101
2008/0015412 A1*  1/2008  Hori ................... A61B 1/00096
                                                                      600/109

(Continued)

FOREIGN PATENT DOCUMENTS

JP          2012-125469 A          7/2012

*Primary Examiner* — Oneal R Mistry
(74) *Attorney, Agent, or Firm* — Oblon, McClelland, Maier & Neustadt, L.L.P.

(57) ABSTRACT

There is provided an image processing device including a detection unit configured to detect a mask from an acquired image, a determination unit configured to determine whether there is a change in the mask detected by the detection unit, and an output unit configured to output a parameter when the determination unit determines that there is a change in the mask, the parameter being related to the mask detected by the detection unit before it is determined that there is a change in the mask.

23 Claims, 11 Drawing Sheets

(56) References Cited

U.S. PATENT DOCUMENTS

| | | | |
|---|---|---|---|
| 2012/0148139 A1* | 6/2012 | Ozawa | A61B 6/504 |
| | | | 382/132 |
| 2012/0188351 A1* | 7/2012 | Kaku | G06T 7/0016 |
| | | | 348/65 |
| 2013/0329019 A1* | 12/2013 | Matsuoka | H04N 13/218 |
| | | | 348/49 |
| 2014/0267220 A1* | 9/2014 | Mehta | G06T 19/20 |
| | | | 345/419 |
| 2015/0057653 A1 | 2/2015 | Sugiyama | |
| 2015/0141753 A1* | 5/2015 | Kanamori | H01L 27/14627 |
| | | | 600/109 |
| 2015/0148594 A1 | 5/2015 | Tadano | |

* cited by examiner

IMAGE PROCESSING DEVICE AND IMAGE PROCESSING METHOD

CROSS REFERENCE TO RELATED APPLICATIONS

This application is a continuation of U.S. patent application Ser. No. 14/625,052, filed Feb. 18, 2015, which claims the benefit of Japanese Priority Patent Application JP 2014-032809 filed Feb. 24, 2014. The entire contents of these applications are incorporated herein by reference.

BACKGROUND

The present technology relates to an image processing device and an image processing method and, more particularly, the present technology relates to an image processing device and an image processing method, capable of appropriately correcting a mask of an endoscope.

An endoscope is used as a medical instrument that is inserted into the body of a subject such as patients and observes the inside of the body. An image from an endoscope is displayed in the form of a circular frame on a rectangular screen. In such cases, it is necessary to detect an image portion in distinction from a lens barrel portion that is displayed as a portion shaded by a lens barrel.

A mask may be used to distinguish a portion that provides an image obtained by an endoscope for the user from a portion that does not provide an image for the user, and JP 2012-125469A discloses a method of detecting a mask of an endoscope.

A mask of an endoscope is detected and software processing is allowed to be performed only in a mask that is an effective area, and thus it is possible to reduce the amount of calculation and to minimize the adverse effects associated with a peripheral portion of a mask in a filter processing and other like processing.

SUMMARY

The coupling between an endoscope and a camera head may be loose, and thus the endoscope is likely to be shifted or rotated during surgery. To solve this, it is necessary to detect a mask for every frame or at every certain interval.

However, as disclosed in JP 2012-125469A, if it is intended to detect a mask from an endoscopic image obtained by capturing the inside of the body, erroneous detection may be caused depending on conditions of an endoscopic image, for example, inaccurate capturing of boundary between a mask and other portions, existence of obstacles such as bubbles, and adhesion of dirt on a lens.

In this way, the position of a mask of an endoscope may be shifted, and thus it is desirable to detect and correct a mask in such a case when the position is shifted.

The present technology is made in view of such circumstances, and it is intended that the correction of a mask is allowed to be performed with accuracy.

According to an embodiment of the present disclosure, there is provided an image processing device including a detection unit configured to detect a mask from an acquired image, a determination unit configured to determine whether there is a change in the mask detected by the detection unit, and an output unit configured to output a parameter when the determination unit determines that there is a change in the mask, the parameter being related to the mask detected by the detection unit before it is determined that there is a change in the mask.

The determination unit may determine whether there is a change in the mask based on a temporal change in a parameter of the mask detected by the detection unit.

The determination unit may determine that there is no change in the mask detected by the detection unit when a difference between a parameter of a first mask detected by the detection unit and a parameter of a second mask detected by the detection unit after the first mask is detected is less than a predetermined threshold. The output unit may output a parameter of a third mask when the determination unit determines that there is no change in the mask, the parameter of the third mask being calculated from the parameter of the first mask and the parameter of the second mask.

The determination unit may determine that there is a change in the mask detected by the detection unit when a difference between a parameter of a first mask detected by the detection unit and a parameter of a second mask detected by the detection unit after the first mask is detected is greater than or equal to a predetermined threshold. The output unit may output the parameter of the first mask when the determination unit determines that there is a change in the mask.

The output unit may output the parameter of the second mask instead of the parameter of the first mask when the determination unit determines that there is a change in the mask by a predetermined number of times.

The output unit may output a parameter of a third mask calculated from the parameter of the first mask and the parameter of the second mask when the determination unit determines that there is a change in the mask by a predetermined number of times.

An image in the mask may include an image captured by an endoscope.

The image processing device may further includes a correction unit configured to correct a parameter of the mask using a reliability parameter representing reliability of a parameter of the mask.

The detection unit may detect a first mask and a second mask from two respective acquired images. The image processing device may further include a correction unit configured to determine whether at least one of a parameter of the first mask and a parameter of the second mask is to be corrected, based on the parameter of the first mask and the parameter of the second mask.

The correction unit may correct one of the parameter of the first mask and the parameter of the second mask using the other parameter that is set previously, when a difference between the parameter of the first mask and the parameter of the second mask is outside a predetermined range.

The correction unit may perform correction using a reliability parameter representing reliability of each of the parameter of the first mask and the parameter of the second mask when a difference between the parameter of the first mask and the parameter of the second mask is outside a predetermined range.

The determination unit may determine whether there is a change in the mask based on a luminance level of the image.

The determination unit may determine that there is a change in the mask when an average luminance level of the image is less than a predetermined threshold.

The determination unit may determine whether there is a change in the mask based on whether an endoscope is inserted into a trocar.

The determination unit may determine that there is a change in the mask when it is determined that an endoscope is not inserted into a trocar.

The determination unit may determine whether there is a change in the mask based on an external input.

The external input may be provided using a foot switch.

According to another embodiment of the present disclosure, there is provided an image processing method including detecting a mask from an acquired image, determining whether there is a change in the detected mask, and outputting a parameter when it is determined that there is a change in the mask, the parameter being related to the mask detected before it is determined that there is a change in the mask.

In the image processing device and image processing method according to an embodiment of the present technology, a mask is detected from an acquired image, whether there is a change in the detected mask is determined, and when it is determined that there is a change in the mask, a parameter related to the mask detected before it is determined that there is a change in the mask is outputted.

According to an embodiment of the present technology, the correction of a mask is allowed to be performed with accuracy.

Note that the advantages herein are not necessarily intended to be restrictive, and any other advantage described in the present disclosure may be achievable.

DETAILED DESCRIPTION OF THE EMBODIMENT(S)

Figure 1:
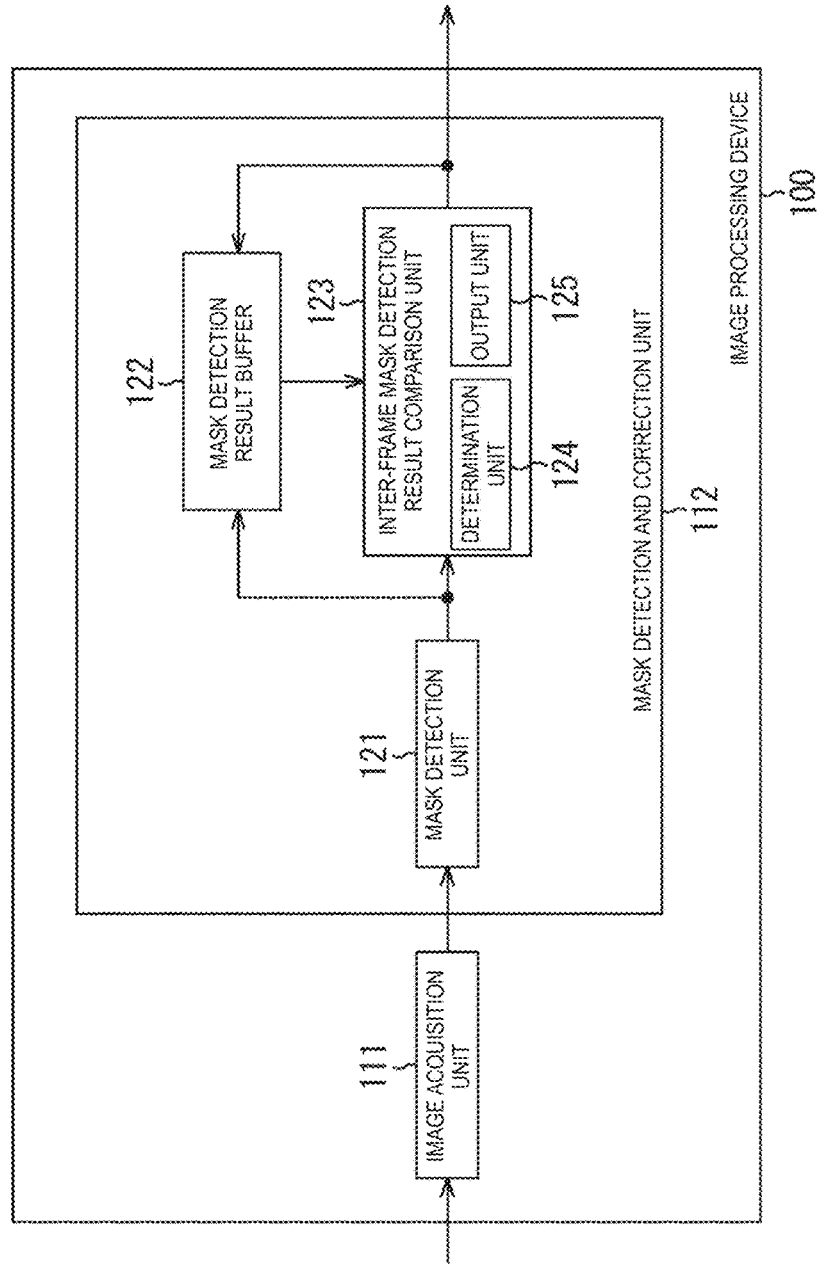
FIG. 1 is a diagram illustrating the configuration of an embodiment of an image processing device to which the present technology is applied.

Embodiments for implementing the present technology (hereinafter simply referred to as "embodiment") will be described. The description will be made in the following order.

1. Configuration of image processing device according to first embodiment

2. Operation by image processing device according to first embodiment

3. Configuration of image processing device according to second embodiment

4. Operation by image processing device according to second embodiment

5. When operation is started

6. Recording medium

<Configuration of Image Processing Device According to First Embodiment>

An image processing device described herein is an image processing device for processing an image obtained from, for example, an endoscope. The present technology described herein may be applied to any device for acquiring an image and detecting a mask from the acquired image other than the device for processing an image obtained from an endoscope. The following description will be made by taking, as an example, an image processing device for processing an image obtained from an endoscope.

FIG. 1 is a diagram illustrated to describe the configuration of an image processing device according to a first embodiment. The image processing device 100 shown in FIG. 1 acquires image data from an endoscopic device (not shown) used as medical instruments, processes the acquired image, and outputs the processed image to a display unit 101 (shown in FIG. 2) such as a monitor for displaying the image.

The image processing device 100 shown in FIG. 1 is configured to include an image acquisition unit 111 and a mask detection and correction unit 112. The mask detection and correction unit 112 is configured to include a mask detection unit 121, a mask detection result buffer 122, and an inter-frame mask detection result comparison unit 123.

The image acquisition unit 111 of the image processing device 100 acquires an image from an endoscopic device (not shown). The endoscopic device is configured to include an endoscope, a light source unit, an imaging means, and a camera control unit. The endoscope forms an in-vivo imaging device inserted into the body cavity for capturing the inside of the body. The light source unit supplies illumination light to the endoscope. The imaging means of the endoscope may be a charge-coupled device (CCD). The camera control unit performs signal processing for the imaging means. The image acquisition unit 111 acquires image data outputted from the camera control unit.

Figure 2:
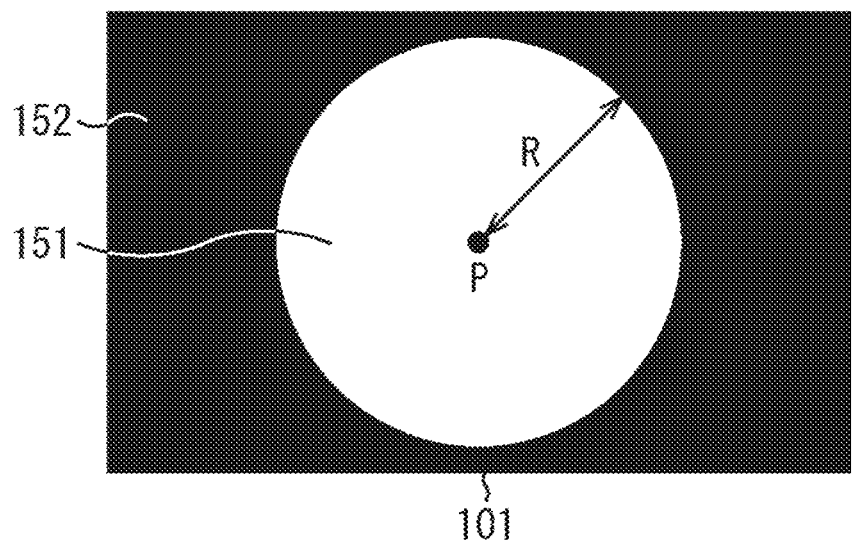
FIG. 2 is a diagram illustrated to describe a mask.

The image data acquired by the image acquisition unit 111 is supplied to the mask detection unit 121 of the mask detection and correction unit 112. A detailed description of a mask is given with reference to FIG. 2. FIG. 2 illustrates an example of an image displayed on the display unit 101. The central region of the screen is a circular effective region 151, which presents an image captured by the endoscopic device to the user.

As shown in FIG. 2, in an image obtained from the endoscope, there is a region in which an in-vivo image is invisible at left, right, upper and lower parts of the image. This is because there is a region in which light is not transmitted to the imaging means due to the existence of vignetting in the endoscope. The region in which an in-vivo image is invisible is referred to as a mask region 152.

The shape of the boundary between the mask region 152 and an effective region 151 in which an in-vivo image is visible is referred to as a mask shape. In the example of the screen shown in FIG. 2, a mask shape is circular. The following description will be made on the assumption that a mask shape is a perfect circle, but the present technology is applicable to other shapes including an ellipse. As shown in FIG. 2, the following description will be made on the assumption that the center of the circle is set to center point P, coordinates of the center point are set to (X,Y), and the radius of the circle is set to R.

The mask detection unit 121 of the image processing device 100 detects the shape of the boundary between the effective region 151 and the mask region 152, that is, in this case, parameters of the coordinates (X,Y) and radius R of the center point P of the circle.

For example, the mask detection unit 121 detects an edge on the boundary between a mask and in-vivo information in the image, performs the Hough transform on the edge by setting the detected edge as a candidate point, estimates a circle (mask), and then detects a mask. For the mask detection unit 121 to detect a mask, any detection method may be employed.

Erroneous detection of a mask by the mask detection unit 121 may be caused by obtaining a low number of edges on the boundary between the mask region 152 and an in-vivo region (effective region 151) that is insufficient to perform detection, when contrast of a captured endoscopic image is insufficient due to a lack of amount of light or depending on the color of an in-vivo object to be captured.

Thus, the mask detection and correction unit 112 is configured to include the mask detection result buffer 122 and the inter-frame mask detection result comparison unit 123 to correct a mask detected by the mask detection unit 121.

A mask detection result outputted from the mask detection unit 121 is supplied to the mask detection result buffer 122 and the inter-frame mask detection result comparison unit 123. The result outputted from the mask detection unit 121 is delayed by one frame and is stored in the mask detection result buffer 122.

The inter-frame mask detection result comparison unit 123 is configured to include a determination unit 124 and an output unit 125. The inter-frame mask detection result comparison unit 123 compares a mask detection result of an image at the current time t and a mask detection result at time t−1 stored in the mask detection result buffer 122, which will be described later in detail. Then, the inter-frame mask detection result comparison unit 123 determines whether there is a change in the mask depending on the absolute value of the difference between two mask detection results, corrects the mask if necessary, and outputs the mask detection result.

The description will be continued on the assumption that the result outputted from the mask detection unit 121 is delayed by one frame and stored in the mask detection result buffer 122. In addition, the description will be continued on the assumption that a process described below is performed for every frame. However, the present technology is not limited to the case in which a process is performed for every frame, but may be configured to perform a process for every several frames.

As described later, the inter-frame mask detection result comparison unit 123 may be configured to perform a process if a predetermined condition is met and to output a mask shape.

<Operation by Image Processing Device According to First Embodiment>

Figure 3:
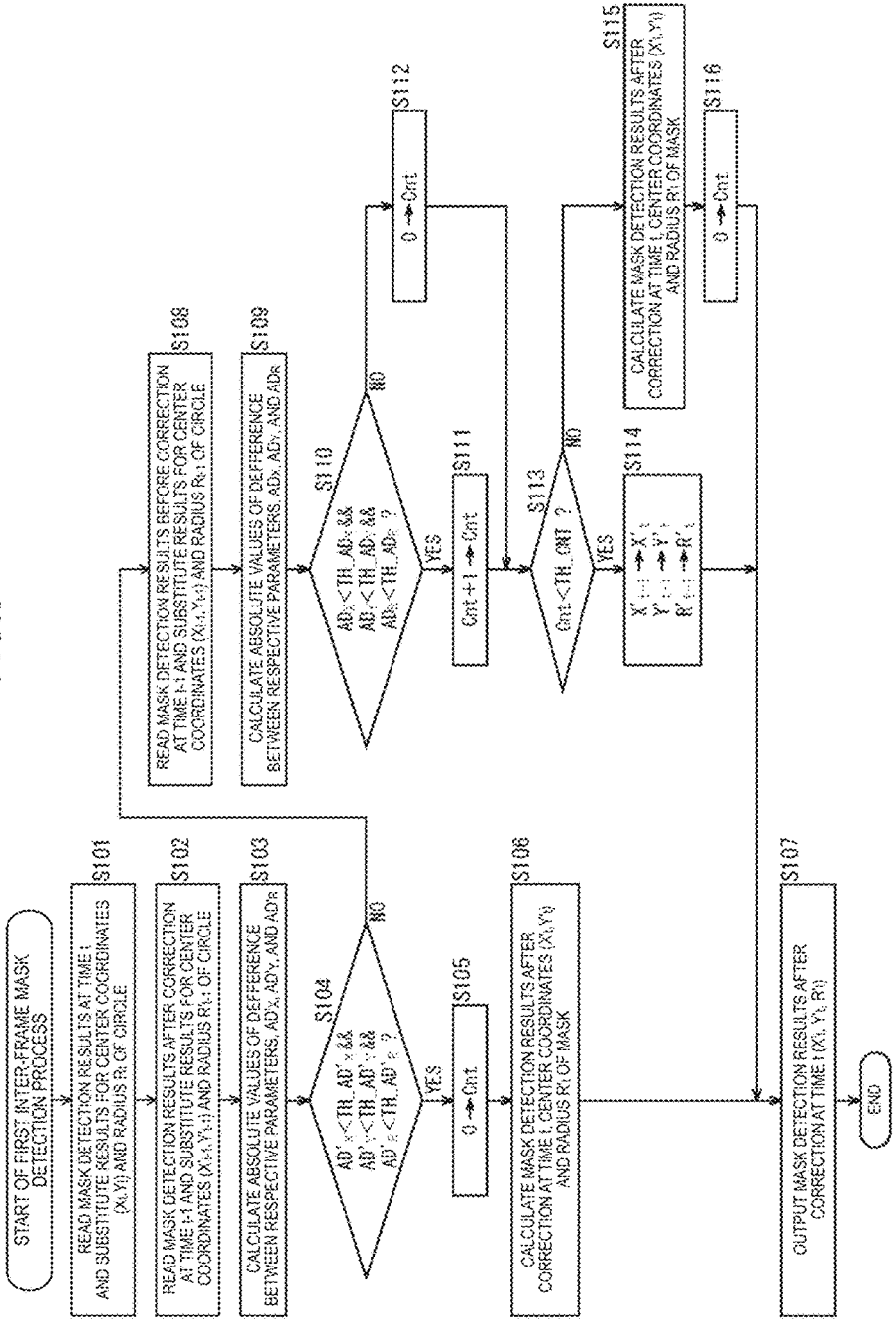
FIG. 3 is a flowchart illustrated to describe the operation performed by the image processing device.

Referring to the flowchart of FIG. 3, the operation by the image processing device 100 shown in FIG. 1 is described. Specifically, the operation performed by the inter-frame mask detection result comparison unit 123 of the mask detection and correction unit 112 is mainly described.

The process shown in the flowchart of FIG. 3 is started on the basis of the assumption that the mask detection result buffer 122 stores a detection result which is obtained from a process performed by the mask detection unit 121 and delayed by at least one frame and stores a correction result which is obtained from a process performed by the inter-frame mask detection result comparison unit 123 and delayed by at least one frame.

In step S101, the inter-frame mask detection result comparison unit 123 reads a mask shape from the mask detection unit 121. The information to be read as a mask shape includes information regarding the coordinates $(X_t, Y_t)$ of the center point of the circle and information regarding the radius $R_t$ of the circle.

In the following description, information of a mask shape that is detected at time t is represented by adding the letter t, for example, $X_t$, $Y_t$, and $R_t$. Information of a mask shape that is detected at the time of the frame immediately preceding the time t is represented by adding the letter t−1, for example, $X_{t-1}$, $Y_{t-1}$, and $R_{t-1}$.

In step S102, the inter-frame mask detection result comparison unit 123 reads a mask detection result after correction at time t−1 (the center $(X'_{t-1}, Y'_{t-1})$ and radius $R'_{t-1}$ of the circle) from the mask detection result buffer 122.

The mask detection result buffer 122 stores information with regard to a mask shape from the mask detection unit 121 and information with regard to a mask shape from the inter-frame mask detection result comparison unit 123.

In the following description, information, which is supplied from the mask detection unit 121 and stored in the mask detection result buffer 122, is represented by adding the letter t−1, for example, the center $(X_{t-1}, Y_{t-1})$ and radius $R_{t-1}$ of the circle. Information, which is supplied from the inter-frame mask detection result comparison unit 123 and stored in the mask detection result buffer 122, is represented by further adding the prime symbol, for example, the center $(X'_{t-1}, Y'_{t-1})$, and radius $R'_{t-1}$ of the circle.

In step S103, the absolute values of the differences between respective parameters of both, $AD'_X$, $AD'_Y$, and $AD'_R$ are calculated based on the following Equations (1) to (3). Here, $AD'_X$ indicates the absolute value of the difference between x-coordinate $X_t$ of the center point of the mask detected at time t and x-coordinate $X'_{t-1}$ of the center point of the mask after correction at time t−1.

Similarly, $AD'_Y$ indicates the absolute value of the difference between y-coordinate $Y_t$ of the center point of the mask detected at time t and y-coordinate $Y'_{t-1}$ of the center point of the mask after correction at time t−1. In addition, $AD'_R$ indicates the absolute value of the difference between the radius $R_t$ of the center point of the mask detected at time t and the radius $R'_{t-1}$ of the center point of the mask after correction at time t−1.

$$AD'_X = |X_t - X'_{t-1}| \tag{1}$$

$$AD'_Y = |Y_t - Y'_{t-1}| \tag{2}$$

$$AD'_R = |R_t - R'_{t-1}| \tag{3}$$

In step S104, it is determined whether the absolute value of the difference between respective parameters is less than a predetermined threshold that is set for each parameter. In other words, it is determined whether the following Equations, that is, three inequalities (4) to (6) are established. In the three inequalities (4) to (6), the threshold $TH\_AD'_X$ is a threshold for the absolute value of x-coordinate of the center point, the threshold $TH\_AD'_Y$ is a threshold for the absolute value of y-coordinate of the center point, and the threshold $TH\_AD'_R$ is a threshold for the absolute value of the radius R.

Absolute value of x-coordinate of center point,
$$AD'_X < \text{Threshold}, TH\_AD'_X \tag{4}$$

Absolute value of y-coordinate of center point,
$$AD'_Y < \text{Threshold}, TH\_AD'_Y \tag{5}$$

Absolute value of radius R, $AD'_R$<Threshold,
$$TH\_AD'_R \tag{6}$$

If it is determined that the three inequalities (4) to (6) are all established in step S104, then the process proceeds to step S105. In step S105, a count value is set to zero. The count value is incremented when any one of the three inequalities (4) to (6) is not established, and is incremented when the mask shape is likely to be changed.

Any one of the three inequalities (4) to (6) is not established when there is a change in the detected mask shape. As described above, erroneous detection of a mask by the mask detection unit 121 may be caused by obtaining a low number of edges on the boundary between the mask region 152 and an in-vivo region (effective region 151) that is insufficient to perform detection, when contrast of a captured endoscopic image is insufficient due to a lack of amount of light or depending on the color of an in-vivo object to be captured.

If a mask shape is changed for some reasons, parameters of the coordinates or radius of the center point of the mask shape outputted as a mask shape at time t−1 have different values from parameters obtained at time t. Thus, the difference between a parameter of the corrected mask shape at time t−1 and a parameter of the mask shape detected at time t increases as the change in a mask shape increases.

For this reason, it can be determined that there is no change in a mask shape when the three inequalities (4) to (6) are all established (condition in which the amount of change is small even if there is a change). It can be determined that there is a change in a mask shape when any one of the three inequalities (4) to (6) is not established.

In step S105, the count value (Cnt), which is set to zero, represents the number of times the mask shape is determined to be changed. Thus, in step S105, it is determined that there is no change in a mask shape in step S104, and thus the count value is set to zero.

In step S106, a weighted average between a detection result obtained by the mask detection unit 121 at time t and a mask detection result after correction at time t−1 is calculated based on the following Equations (7) to (9), and a mask detection result after correction (center coordinates $(X'_t, Y'_t)$ and radius $R'_t$ of the circle) is determined.

$$X'_t = w_1 X_t + (1-w_1) X'_{t-1} \quad (7)$$

$$Y'_t = w_1 Y_t + (1-w_1) Y'_{t-1} \quad (8)$$

$$R'_t = w_1 R_t + (1-w_1) R'_{t-1} \quad (9)$$

In Equations (7) to (9), w1 represents a weighting factor that satisfies $0 \leq w_1 \leq 1$. If the weighting factor w1 is larger, the allowable range of variations in mask detection results between frames can be set to larger. If the weighting factor w1 is smaller, the allowable range of variations in mask detection results between frames can be set to smaller.

In step S107, the center coordinates $(X'_t, Y'_t)$ and radius $R'_t$ of the circle that are calculated by inter-frame mask detection result comparison unit 123 in step S106 are outputted to the subsequent processing unit (not shown).

In this case, the three inequalities (4) to (6) are all established and at that time it is determined that the mask shape being outputted and mask shape being detected have no significant change, and thus the mask shape detected by the mask detection unit 121 may be outputted to the subsequent processing unit (not shown) without any modification.

In the present embodiment, further in step S106, a correction process to absorb the small amount of change in the mask shape is performed by Equations (7) to (9) and the mask shape obtained by performing such correction process is outputted to the subsequent processing unit. Thus, it is possible to obtain a more accurate mask shape.

On the other hand, if it is determined that any one of the three inequalities (4) to (6) is not established in step S104, the process proceeds to step S108. The process proceeds to step S108 when there is a possibility of a change in a mask shape. In step S108, the inter-frame mask detection result comparison unit 123 reads the mask detection result before correction at time t−1 (the center coordinates $(X_{t-1}, Y_{t-1})$ and radius $R_{t-1}$ of the circle), which is stored in the mask detection result buffer 122.

In step S109, the absolute values of the difference between the respective parameters of the detection result of the mask detection unit 121 at time t (center coordinates $(X_t, Y_t)$ and radius $R_t$ of the circle) and the mask detection result before correction at time t−1 (center coordinates $(X_{t-1}, Y_{t-1})$ and radius $R_{t-1}$ of the circle), $AD_X$, $AD_Y$, and $AD_R$, are calculated based on the following Equations (10) to (12).

$$AD_X = |X_t - X_{t-1}| \quad (10)$$

$$AD_Y = |Y_t - Y_{t-1}| \quad (11)$$

$$AD_R = |R_t - R_{t-1}| \quad (12)$$

In Equations (10) to (12), $AD_X$ represents the absolute value of the difference between respective x-coordinates of the center points of the masks detected at time t and time t−1, $AD_Y$ represents the absolute value of the difference between respective y-coordinates of the center points of the masks detected at time t and time t−1, and $AD_R$ represents the absolute value of the difference between respective radii R of the masks detected at time t and time t−1.

In step S110, it is determined whether the absolute values of the difference between the respective parameters are all less than a predetermined threshold. In other words, it is determined whether the following Equations, that is, three inequalities (13) to (15) are all established.

In the following three inequalities (13) to (15), a threshold $TH\_AD_X$ is a threshold for the absolute value of x-coordinate of the center point, a threshold $TH\_AD_Y$ is a threshold for the absolute value of y-coordinate of the center point, and a threshold $TH\_AD_R$ is a threshold for the absolute value of the radius R.

Absolute value of x-coordinate of center point,
$AD_X$<Threshold, $TH\_AD_X$ (13)

Absolute value of y-coordinate of center point,
$AD_Y$<Threshold, $TH\_AD_Y$ (14)

Absolute value of radius R, $AD_R$<Threshold,
$TH\_AD_R$ (15)

In step S110, if it is determined that the three inequalities (13) to (15) are all established, the process proceeds to step S111. In step S111, the count value is set to a value incremented by one.

On the other hand, in step S110, if it is determined that any one of the three inequalities (13) to (15) is not established, the process proceeds to step S112. In step S112, the count value is set to zero (initialization).

In step S111 or S112, after the count value is set, the process proceeds to step S113. In step S113, it is determined whether the count value Cnt is less than a predetermined threshold TH_CNT.

In step S113, if it is determined that the count value Cnt is less than the predetermined threshold TH_CNT, then the process proceeds to step S114. In step S114, the mask detection result after correction at time t−1 (center coordinates $(X'_{t-1}, Y'_{t-1})$ and radius $R'_{t-1}$ of the circle) is substituted for the mask detection result after correction at time t (center coordinates ($X'_t$, $Y'_t$) and radius $R'_t$ of the circle).

In this case, the parameters of the mask shape after correction outputted to the subsequent stage at time t−1 is set as parameters of the mask shape after correction to be outputted to the subsequent stage at time t. The parameters that are set in this way are outputted to the subsequent processing unit (step S107) and stored in the mask detection result buffer 122 as parameters of the mask shape after correction outputted to the subsequent stage at time t−1.

In this way, the process proceeds to step S114 when, even though there is a possibility of a change in the mask shape, the mask is continued to keep its shape.

On the other hand, in step S113, if it is not determined that the count value Cnt is less than the threshold TH_CNT, the process proceeds to step S115. In step S115, a weighted average between the detection result of the mask detection unit 121 at time t and the mask detection result after correction at time t−1 is calculated, and the mask detection result after correction at time t (center coordinates ($X'_t$, $Y'_t$) and radius $R'_t$ of the circle) is determined.

This calculation is performed based on the following Equations (16) to (18). In Equations (16) to (18), w2 is a weighting factor that satisfies 0≤w2≤1.

$$X'_t = w_2 X_t + (1-w_2) X'_{t-1} \quad (16)$$

$$Y'_t = w_2 Y_t + (1-w_2) Y'_{t-1} \quad (17)$$

$$R'_t = w_2 R_t + (1-w_2) R'_{t-1} \quad (18)$$

The case in which the process proceeds to step S115 corresponds to when it is determined that the changed mask shape is a correct mask shape because the mask shape is continued to be determined to be changed during a predetermined period of time. If the mask shape is immediately modified into the changed mask shape, the mask shape is likely to be abruptly changed, and thus the calculation in step S115 is performed for gradual modification into the changed mask shape.

In step S116, the count value (Cnt) is initialized to zero. Then, in step S107, the center coordinates ($X'_t$, $Y'_t$) and radius $R'_t$ of the circle, which are calculated by Equations (16) to (18), are outputted to the subsequent processing unit and are stored in the mask detection result buffer 122 as parameters of the mask shape after correction which are outputted to the subsequent stage at time t−1.

In this way, when the absolute values of the difference, $AD'_X$, $AD'_Y$, and $AD'_R$, are continuously respectively greater than or equal to the thresholds $TH\_AD'_X$, $TH\_AD'_Y$, and $TH\_AD'_R$, and the absolute values of the difference, $AD_X$, $AD_Y$, and $AD_R$, are continuously respectively less than the thresholds $TH\_AD_X$, $TH\_AD_Y$, and $TH\_AD_R$, over a predetermined period of time (the duration at which the count value is greater than or equal to the threshold TH_CNT), the position of a mask is likely to be physically shifted in the middle of processing.

In such cases, it is necessary to correct the position of a mask to obtain a new position of a mask over a certain period of time. In this case, if the weighting factor w2 increases, the time until the correction to obtain a new position of a mask is performed decreases, and if the weighting factor w2 decreases, the time until the correction to obtain a new position of a mask is performed increases.

The parameters that are set in this way are outputted to the subsequent processing unit as the mask detection result after correction at time t (center coordinates ($X'_t$, $Y'_t$) and radius $R'_t$ of the circle) in step S107, as described above. The mask detection result after correction at time t (center coordinates ($X'_t$, $Y'_t$) and radius $R'_t$ of the circle) is also outputted to the mask detection result buffer 122 and stored therein for use in the next frame.

The above processing will be described in detail with reference to FIGS. 4 and 5.

Figure 4:
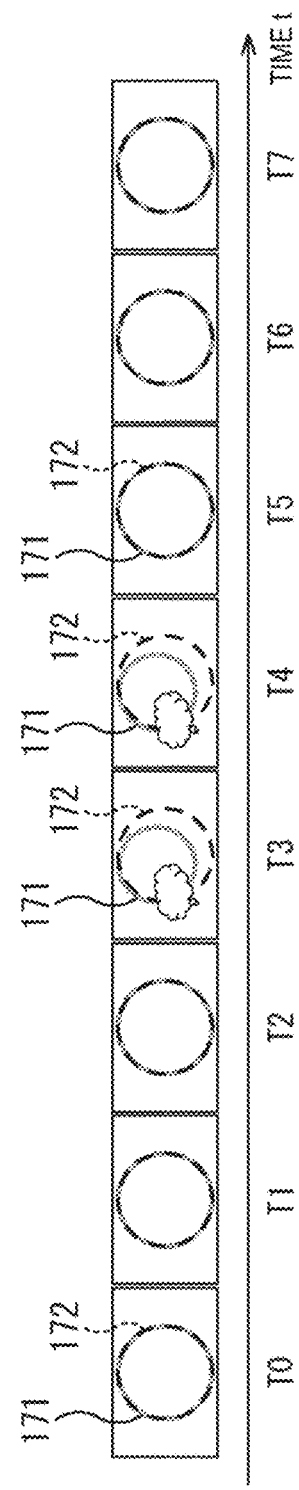
FIG. 4 is a diagram illustrated to describe the correction of a mask shape.
Figure 5:
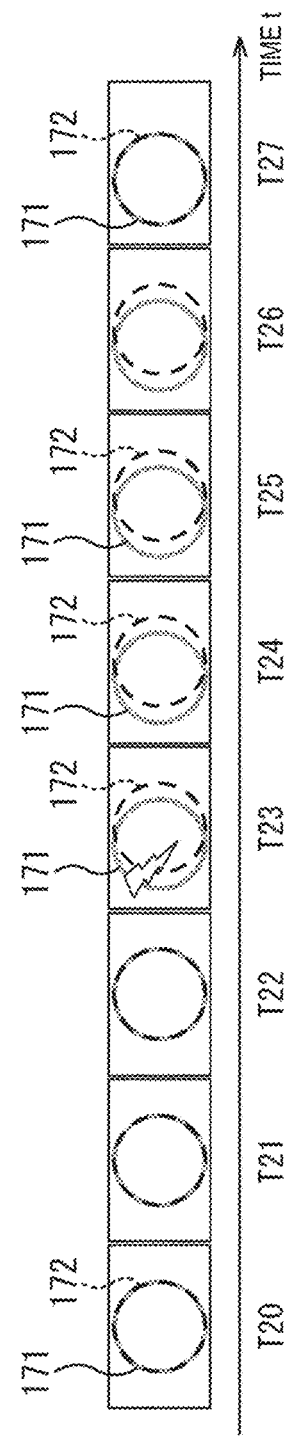
FIG. 5 is a diagram illustrated to describe the correction of a mask shape.

In FIGS. 4 and 5, the horizontal axis t represents time, and images (frames) of the figures are images obtained in the past in the order of time toward the left side. In FIGS. 4 and 5, the mask region 152 is shown without being blackened.

A solid-line circle 171 in the figures represents the result outputted from the mask detection unit 121 (see FIG. 1), and A dotted-line circle 172 in the figures represents the result outputted from the inter-frame mask detection result comparison unit 123 (see FIG. 1).

A cloud-shaped mark in the figures represents a frame in which the image is in a deteriorated condition for some reasons such as adhesion of dust or dirt on the lens included in an endoscopic device and then the accurate mask detection is not allowed to be performed. Such a situation is assumed to be occurred in the frames at time T3 and T4 in the example of FIG. 4.

During the period of time from time T0 to T2 in FIG. 4, the absolute value of the difference between the mask detection result before correction (result outputted from the mask detection unit 121) and the mask detection result after correction in the immediately previous frame is less than a threshold, the mask detection result after correction of the frame at the current time is calculated using Equations (7) to (9).

In other words, during the period of time from time T0 to T2, as shown in FIG. 4, the circle 171 representing the mask detection result before correction and the circle 172 representing the mask detection result after correction are located at substantially the same position.

At time T3, it is assumed that an image is difficult to perform detection of a mask in the image for a reason such as adhesion of dust or dirt on the lens. In this case, the mask detection unit 121 fails to accurately perform detection of a mask, which results in erroneous mask shape result being outputted.

However, the inter-frame mask detection result comparison unit 123 compares the result outputted from the mask detection unit 121 with the mask shape after correction in the immediately previous frame (frame at time T2). Then, the absolute value of the difference between both is greater than or equal to the threshold, and the mask shape after correction at time T2 is outputted from the inter-frame mask detection result comparison unit 123 as a result after correction at time T3.

Referring to the image at time T3 in FIG. 4, the circle 171 representing the mask detection result before correction is shown as a small circle on the left, but the circle 172 representing the mask detection result after correction is the same circle 172 as the circle 172 at time T2.

Here, the description will be made on the assumption that the threshold TH_CNT of the count value (Cnt) is set to five in the flowchart of FIG. 3. At time T4, as in the case of time T3, even when the mask shape result obtained by the mask detection unit 121 is erroneous, the count value (Cnt) is less than the threshold TH_CNT(=5). Thus, the inter-frame mask detection result comparison unit 123 corrects the erroneous mask shape to make the mask shape after correction at time T3.

At time T5, the image is in an improved condition, and the absolute value of the difference between the result outputted from the mask detection unit 121 and the mask shape after correction in the frame at the immediately previous time T4 is less than a threshold. Thus, the mask shape after correction in the frame at the current time T5 is calculated using Equations (7) to (9).

In this way, it is possible to prevent erroneous detection at a given period of time (less than the threshold TH_CNT).

Referring now to FIG. 5, it is assumed that a case in which external force is applied to an endoscope, a connection portion between the endoscope and a camera head is shifted, and thus the mask is deviated from its normal position, or a case in which an endoscope is turned and thus the mask is deviated from its normal position.

In such a case, the mask remains in the deviated position, and thus previous detection of a mask only once is insufficient to detect a mask.

In FIG. 5, when the position of a mask is deviated at time T23 for the reason as described above, the position of a mask (mask shape) before the deviation of its position is outputted as an output result of the inter-frame mask detection result comparison unit 123 during the period of time when the value is less than the threshold TH_CNT.

Referring to the image at time T23 in FIG. 5, the circle 171 representing the mask detection result before correction is deviated to the left side, but the circle 172 representing the mask detection result after correction is located at the same position as the circle 172 at time T22, and thus the mask at the position is presented to the user.

In this regard, when the threshold is set to five (TH_CNT=5), the position of a mask before the deviation of its position is outputted as an output result of the inter-frame mask detection result comparison unit 123 over the period of time from T23 to T26. Then, at time T27, it is not determined that the count value (Cnt) is less than the threshold TH_CNT (=5), the mask detection result after correction is a value calculated by Equations (16) to (18) and a process is started to make it gradually close to the position of a mask after the deviation of its position.

In the example shown at time T27 in FIG. 5, the circle 172 representing the mask detection result after correction is set at substantially the same position as the circle 171 representing the detection result of a mask before correction that is deviated to the left side, and thus the mask at that position is presented to the user.

In this way, when the parameter of the mask shape is set to a value calculated by Equations (16) to (18) and is gradually close to the position of a mask after the deviation of its position, it swiftly converges on the deviated position of a mask as the weighting factor w2 in Equations (16) to (18) increases.

Furthermore, if the threshold TH_CNT is made excessively small, it is possible to swiftly modify the position of a mask to the deviated position of a mask in the case as shown in FIG. 5, but it may be unable to appropriately deal with the erroneous detection in a short time as shown in FIG. 4. On the other hand, if the threshold TH_CNT is made excessively large, it is able to appropriately deal with the erroneous detection in a short time, but in the case as shown in FIG. 5, it takes time to modify the position of a mask. In view of the above, the threshold TH_CNT is set.

At time T0 or time T20, there is no mask shape after correction of the previous frame. In such a case, the result outputted from the mask detection unit 121 at that time may be used without any modification as the result outputted from the inter-frame mask detection result comparison unit 123, or the detection of a mask is performed for an image in which a scene from which a mask is able to be easily detected is captured previously, and the detected mask may be used as the mask shape after correction of the previous frame at time T0 or time T20.

Thus, according to the present embodiment, it is possible to accurately correct a mask shape.

<Configuration of Image Processing Device According to Second Embodiment>

Figure 6:
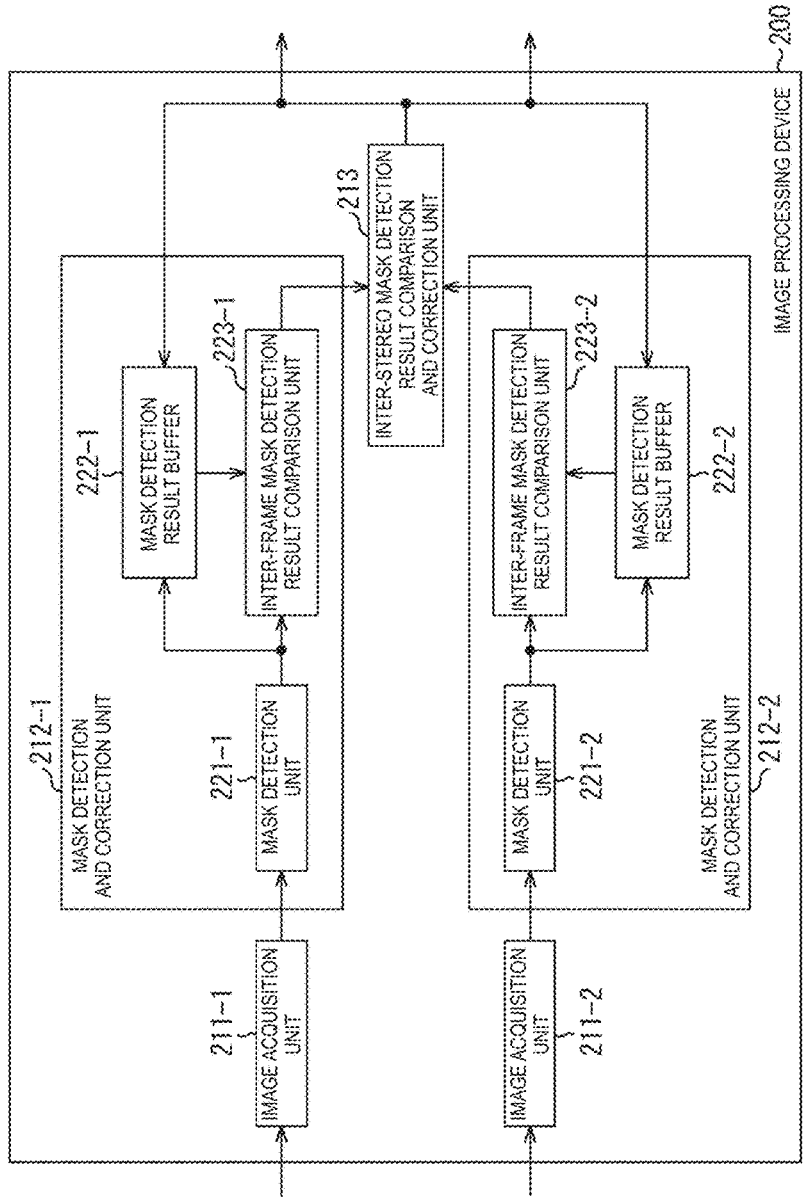
FIG. 6 is a diagram illustrating the configuration of an embodiment of an image processing device to which the present technology is applied.

FIG. 6 is a diagram illustrating the configuration of an image processing device according to a second embodiment. The following description is made on the assumption that the image processing device 200 according to the second embodiment is a device for acquiring an image from an endoscopic device and processing the acquired image, which is similar to the image processing device 100 according to the first embodiment.

The image processing device 200 shown in FIG. 6 is configured to include image acquisition units 211-1 and 211-2, mask detection and correction units 212-1 and 212-2, and an inter-stereo mask detection result comparison and correction unit 213.

The mask detection and correction unit 212-1 is configured to include a mask detection unit 221-1, a mask detection result buffer 222-1, and an inter-frame mask detection result comparison unit 223-1. The mask detection and correction unit 212-2 is configured to include a mask detection unit 221-2, a mask detection result buffer 222-2, and an inter-frame mask detection result comparison unit 223-2.

The image processing device 200 acquires a left-eye image and a right-eye image from an endoscopic device, processes the acquired images, and outputs the processed image to a subsequent processing unit (not shown). Thus, a portion for processing the left-eye image and a portion for processing the right-eye image are provided, and the portion for processing the left-eye image has a substantially similar configuration to that of the portion for processing the right-eye image.

The following description will be made on the assumption that, when there is no necessity for a distinction between the portion for processing the left-eye image and the portion for processing the right-eye image, either one of them is given as an example. In addition, for example, when there is no necessity for a distinction between the image acquisition unit 211-1 and the image acquisition unit 211-2, these units will be simply referred to as image acquisition unit 211 in the following description. This is similarly applied to other components.

The combination of the image acquisition unit 211 and the mask detection and correction unit 212 has a similar configuration to that of the combination of the image acquisition unit 111 and the mask detection and correction unit 112 of the image processing device 100 according to the first embodiment illustrated in FIG. 1, and substantially similar processing is performed by them. Thus, the detailed description thereof is omitted.

Figure 7:
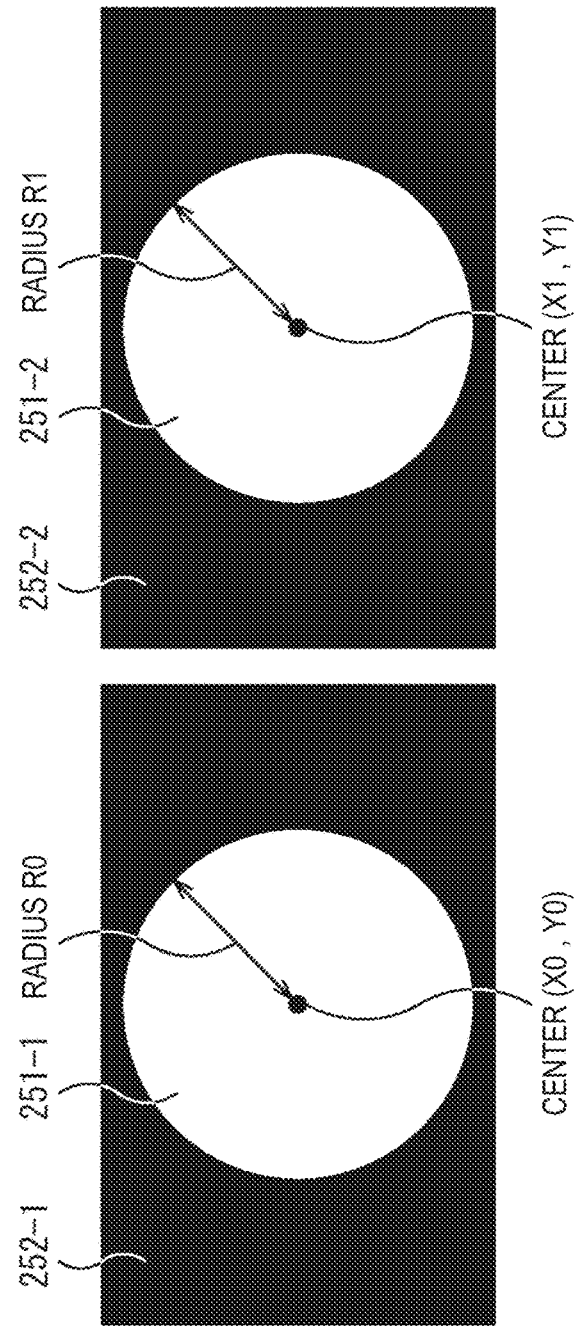
FIG. 7 is a diagram illustrated to describe a mask.

The image processing device 200 shown in FIG. 6 is used for a monocular stereo endoscope, and thus two endoscopic images for the left and right eyes are obtained. The following description is made on the assumption that the center coordinates of the mask shape 252-1 in the endoscopic image for the left eye is set to coordinates (X0, Y0) and the radius thereof is set to radius R0, and the center coordinates of the mask shape 252-2 in the endoscopic image for the right eye is set to coordinates (X1, Y1) and the radius thereof is set to radius R1, as shown in FIG. 7.

An amount of deviation (X0-X1) in the horizontal direction of the center (center of the circle) of a mask of the left- and right-eye images is typically constant, and thus it may be possible to measure the amount of deviation in advance.

In addition, when the amount of deviation is changed, the distance between the centers of a mask of the left- and right-eye images may be measured dynamically.

In the image processing device 200, the endoscopic image for the left eye is acquired by the image acquisition unit 211-1 and is supplied to the mask detection unit 221-1. The mask detection unit 221-1 outputs information regarding the mask shape in the endoscopic image for the left eye to the mask detection result buffer 222-1 and the inter-frame mask detection result comparison unit 223-1.

The inter-frame mask detection result comparison unit 223-1 is configured to include a determination unit and an output unit (both not shown), in the same way to the inter-frame mask detection result comparison unit 123 according to the first embodiment. The inter-frame mask detection result comparison unit 223-1 corrects a mask shape in consideration of consistency in the detection results between frames using the supplied information regarding the mask shape, and outputs information regarding the corrected mask shape to the inter-stereo mask detection result comparison and correction unit 213.

As described later, the inter-frame mask detection result comparison unit 223-1 generates a reliability parameter and outputs the generated reliability parameter to the inter-stereo mask detection result comparison and correction unit 213.

The inter-frame mask detection result comparison unit 223-1 performs a comparison with the mask shape after correction at time t−1 ($X'_{t-1}$, $Y'_{t-1}$, $R'_{t-1}$) in the processing by the inter-frame mask detection result comparison unit.

The first embodiment is different from the second embodiment in that the mask shape after correction at time t−1 in the first embodiment is the result outputted from the inter-frame mask detection result comparison unit 123 at time t−1, but the mask shape after correction at time t−1 in the second embodiment is the result outputted from the inter-stereo mask detection result comparison and correction unit 213.

Similarly, in the image processing device 200, an endoscopic image for the left eye is acquired by the image acquisition unit 211-2 and is supplied to the mask detection unit 221-2. The mask detection unit 221-2 outputs information regarding the mask shape in the endoscopic image for the right eye to the mask detection result buffer 222-2 and the inter-frame mask detection result comparison unit 223-2.

The inter-frame mask detection result comparison unit 223-2 corrects a mask shape in consideration of consistency in the detection results between frames using the supplied information regarding the mask shape and outputs information regarding the corrected mask shape to the inter-stereo mask detection result comparison and correction unit 213, in the same way to the inter-frame mask detection result comparison unit 123 in the first embodiment.

As described later, the inter-frame mask detection result comparison unit 223-2 generates a reliability parameter and outputs the generated reliability parameter to the inter-stereo mask detection result comparison and correction unit 213.

The inter-stereo mask detection result comparison and correction unit 213 compares the mask detection result in the left endoscopic image and the mask detection result in the right endoscopic image, and corrects the result outputted from the inter-frame mask detection result comparison unit 223 depending on the magnitude of the absolute value of the difference between them.

<Operation by Image Processing Device According to Second Embodiment>

Figure 8:
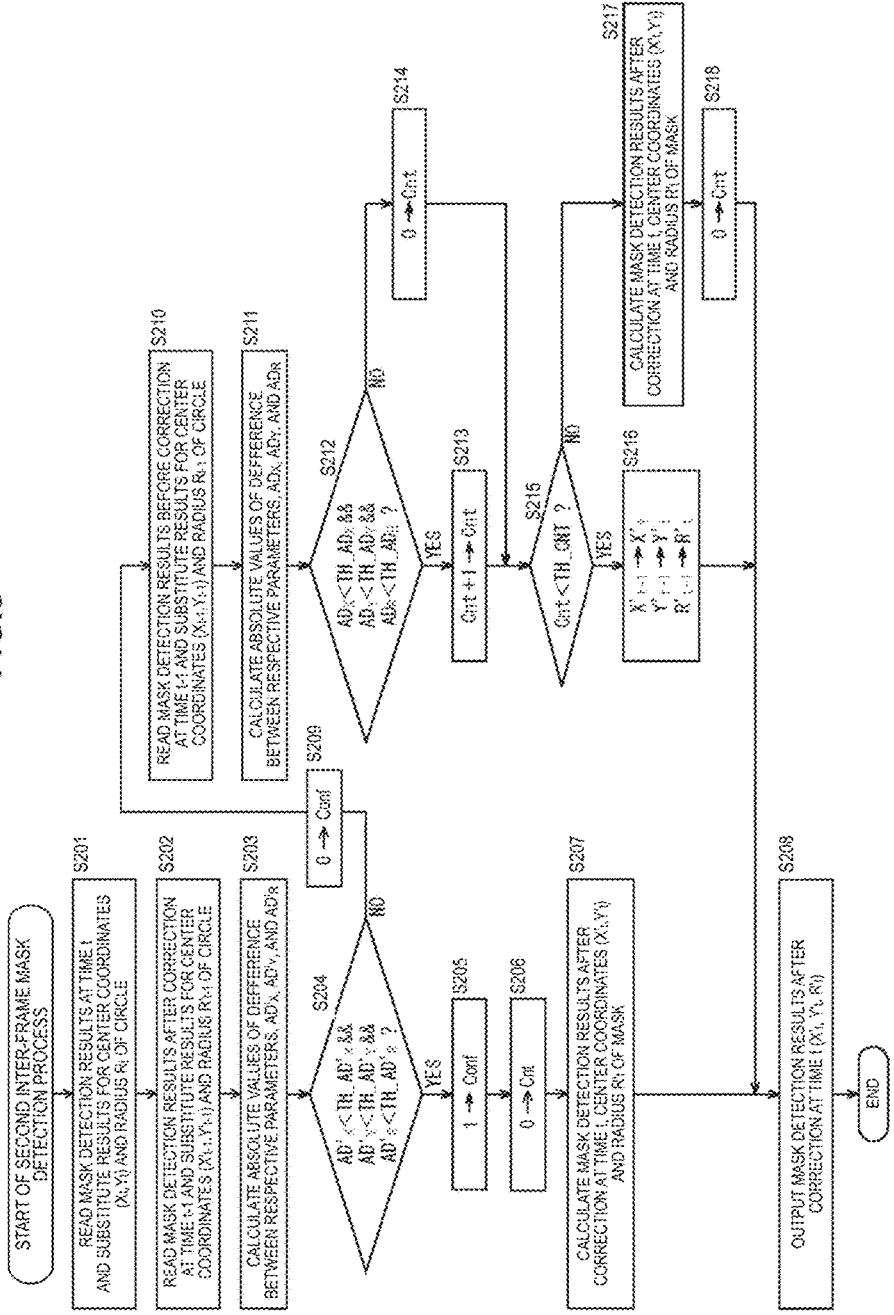
FIG. 8 is a flowchart illustrated to describe the operation performed by the image processing device.

Referring to the flowchart of FIG. 8, the operation performed by the image processing device 200 shown in FIG. 6 is described. Specifically, the operation performed by the inter-frame mask detection result comparison unit 223 of the mask detection and correction unit 212 is mainly described.

The operation performed by the inter-frame mask detection result comparison unit 223 is performed in a substantially similar way to the operation performed by the inter-frame mask detection result comparison unit 123 according to the first embodiment. The difference between them is that a reliability parameter is calculated and outputted, and thus the description is made about the difference.

Processing in steps S201 to S204 is similar to that in steps S101 to S104 of the flowchart shown in FIG. 3, processing in steps S206 and S207 is similar to that in steps S105 and S106, and processing in steps S210 to S218 is similar to that in steps S108 to S116. Thus, the repeated description will be omitted.

In step S204, if it is determined that the inequalities (4) to (6) are all established, then the process proceeds to step S205. In step S205, the reliability parameter (Conf) is set to one. The following will be described on the assumption that the reliability parameter is set to one if the mask shape to be outputted (parameter regarding a mask) is more likely to be correct, but the reliability parameter is set to zero if the mask shape to be outputted is less likely to be correct.

In other words, the reliability parameter is set to one if it is determined that the mask shape after correction outputted from the inter-frame mask detection result comparison unit 213 is substantially consistent with the mask shape detected by the mask detection unit 221 (the inequalities (4) to (6) are all established) and the mask shape is not changed. The reliability parameter is set to zero if it is determined that the mask shape is likely to be changed.

In this regard, the following description will be given on the assumption that the reliability parameter is set to zero or one, but the condition in which the reliability parameter may be set to zero or one may be reversed. In addition, the reliability parameter may be set to a value other than zero or one. For example, the reliability parameter may be set to a value corresponding to the possibility that the mask shape is changed.

In step S208, the reliability parameter that is set in this way is outputted to the inter-stereo mask detection result comparison and correction unit 213 together with the mask detection result after correction at time t.

On the other hand, in step S204, if a condition that the inequalities (4) to (6) are all established is determined not to be satisfied, then the process proceeds to step S209. In step S209, the reliability parameter (Conf) is set to zero. In this case, the mask shape is likely to be changed, and thus the reliability parameter is set to zero.

After step S209, processing in step S210 and the subsequent steps are substantially similar to that of the first embodiment, thus a description thereof will be omitted.

As described above, the inter-frame mask detection result comparison unit 223-1 processes an image for the left eye and supplies the mask detection result after correction and the reliability parameter to the inter-stereo mask detection result comparison and correction unit 213. Similarly, as described above, the inter-frame mask detection result comparison unit 223-2 processes an image for the right eye and supplies the mask detection result after correction and the reliability parameter to the inter-stereo mask detection result comparison and correction unit 213.

Figure 9:
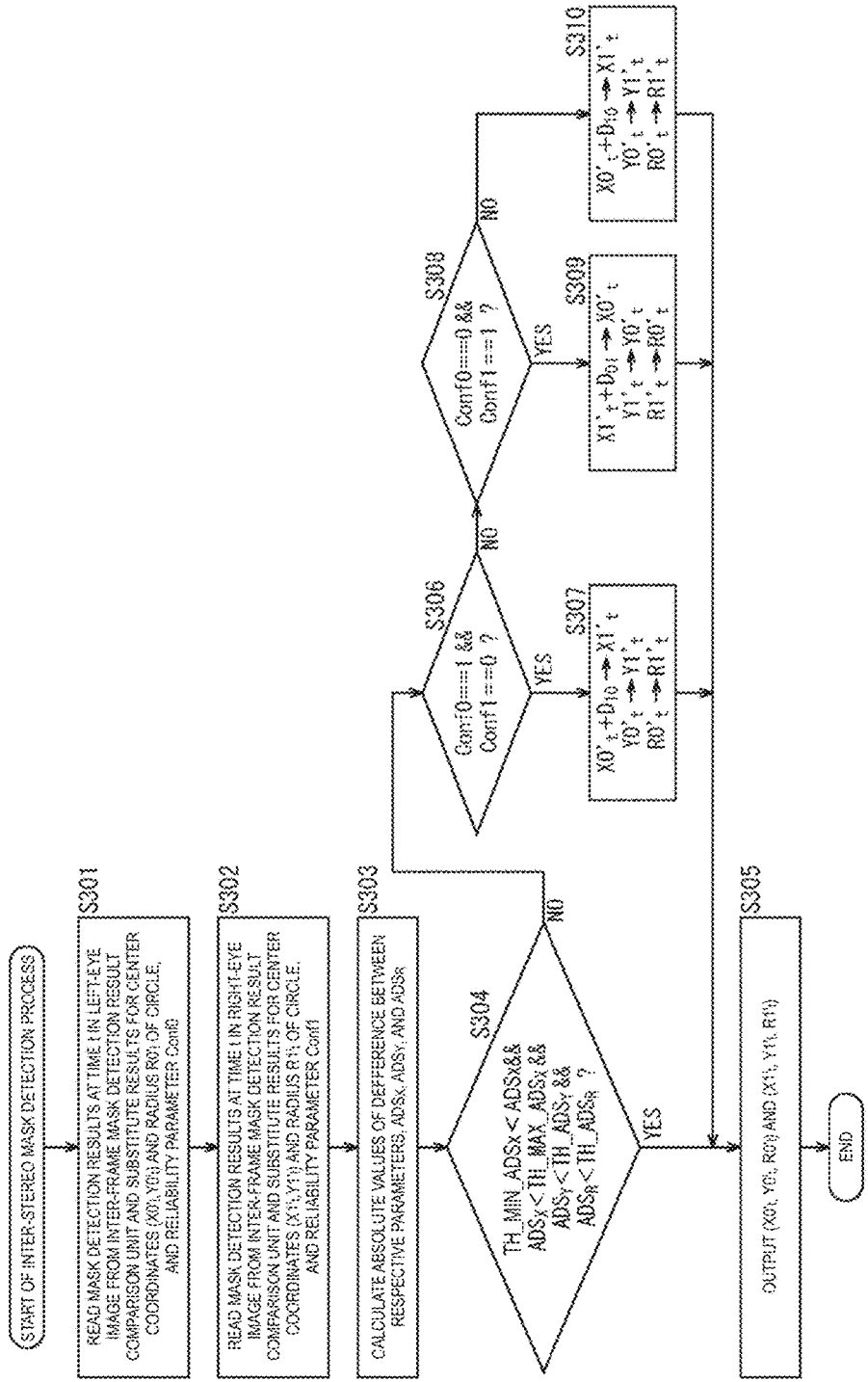
FIG. 9 is a flowchart illustrated to describe the operation performed by the image processing device.

Referring now to the flowchart of FIG. 9, the operation performed by the inter-stereo mask detection result comparison and correction unit 213 is described.

In step S301, a reliability parameter Conf0 and information regarding the mask shape after correction (X0'$_t$, Y0'$_t$, R0'$_t$) in the endoscopic image for the left eye outputted from the inter-frame mask detection result comparison unit 223-1 are obtained.

In step S302, a reliability parameter Conf1 and information regarding the mask shape after correction (X1'$_t$, Y1'$_t$, R1'$_t$) in the endoscopic image for the left eye are obtained.

In step S303, the absolute value of the difference between the acquired respective parameters, ADS$_X$, ADS$_Y$, and ADS$_R$ are calculated based on the following Equations (19) to (21).

In the following Equations (19) to (21), ADS$_X$ represents the absolute value of the difference between x-coordinates of the center point of the mask shape for the left eye and the right eye after correction, ADS represents the absolute value of the difference between y-coordinates of the center point of the mask shape for the left eye and the right eye after correction, and ADS$_R$ represents the absolute value of the difference between the radii R of the mask shape for the left eye and the right eye after correction.

$$ADS_X = |X0'_t - X1'_t| \quad (19)$$

$$ADS_Y = |Y0'_t - Y1'_t| \quad (20)$$

$$ADS_R = |R0'_t - R1'_t| \quad (21)$$

In step S304, it is determined whether the following Equations, that is, inequalities (22) to (25) are all established. In the inequalities (22) to (25), the thresholds TH_MIN_ADS$_X$ and TH_MAX_ADS$_X$ are threshold values for the absolute value of x-coordinate of the center point. The threshold TH_ADS$_Y$ is a threshold for the absolute value of y-coordinate of the center point, and the threshold TH_ADS$_R$ is a threshold for the absolute value of the radius R.

Threshold, TH_MIN_ADS$_X$<Absolute value of x-coordinate of center point, ADS$_X$ (22)

Absolute value of x-coordinate of center point, ADS$_X$<Threshold, TH_MAX_ADS$_X$ (23)

Absolute value of y-coordinate of center point, ADS$_Y$<Threshold, TH_ADS$_Y$ (24)

Absolute value of radius R, ADS$_R$<Threshold, TH_ADS$_R$ (25)

In step S304, if it is determined that Equations (22) to (25) are all established, the process proceeds to step S305. In other words, this case occurs when the absolute value of the difference ADS$_X$ is greater than or equal to the threshold TH_MIN_ADS$_X$ and less than the threshold TH_MAX_ADS$_X$ and when the absolute values of the difference ADS and ADS$_R$ are less than the thresholds TH_ADS$_Y$ and TH_ADS$_R$, respectively.

In such cases, in step S305, the results outputted from the inter-frame mask detection result comparison unit 223-1 and the inter-frame mask detection result comparison unit 223-2 are outputted, without any modification, from the inter-stereo mask detection result comparison and correction unit 213.

In step S304, if a condition that Equations (22) to (25) are all established is determined not to be satisfied, the process proceeds to step S306. In step S306, the reliability parameter Conf0 from the inter-frame mask detection result comparison unit 223-1 and the reliability parameter Conf1 from the inter-frame mask detection result comparison unit 223-2 are compared with each other.

In step S306, it is determined whether the reliability parameter of the left-eye image Conf0 is set to one and whether the reliability parameter of the right-eye image Conf1 is set to zero. If such a condition is satisfied, it can be determined that the result in the left-eye image outputted from the inter-frame mask detection result comparison unit 223-1 is more reliable than the result in the right-eye image outputted from the inter-frame mask detection result comparison unit 223-2.

In step S306, if it is determined that the reliability parameter of the left-eye image Conf0 is set to one and the reliability parameter of the right-eye image Conf1 is set to zero, the process proceeds to step S307.

In step S307, as a mask shape after correction for the left-eye image from the inter-stereo mask detection result comparison and correction unit 213, the result (X0'$_t$, Y0'$_t$, R0'$_t$) outputted from the inter-frame mask detection result comparison unit 223-1 is outputted without any modification. In this case, the mask shape in the left-eye image from the inter-frame mask detection result comparison unit 223-1 is used without any modification because it is more likely to be correct.

On the other hand, parameters of the mask shape after correction in the right-eye image are calculated based on the following Equations (26) to (28).

$$X1'_t = X0'_t \pm D_{10} \quad (26)$$

$$Y1'_t = Y0'_t \quad (27)$$

$$R1'_t = R0'_t \quad (28)$$

In Equation (26), $D_{10}$ represents the distance between the centers of the mask for the left- and right-eye images, as shown in the following Equation (29).

$$D_{10} = X1 - X0 \quad (29)$$

In Equation (29), X0 represents x-coordinate of the center point of the mask shape for the left-eye image at a given time, and X1 represents x-coordinate of the center point of the mask shape for the right-eye image at a given time. For example, X0 and X1 may be previously determined, or they may be calculated when the reliability parameter for the left-eye image Conf0 of the inter-frame mask detection result comparison unit 223-1 and the reliability parameter for the right-eye image Conf1 of the inter-frame mask detection result comparison unit 223-2 are all set to one.

The parameters of the mask shape after correction in the right-eye image calculated in step S307 and the result outputted from the inter-frame mask detection result comparison unit 223-1 that is set as the mask shape after correction for the left-eye image are outputted to the subsequent processing unit, in step S305.

On the other hand, in step S306, if a condition that the reliability parameter of the left-eye image Conf0 is set to one and the reliability parameter of the right-eye image Conf1 is set to zero is determined not to be satisfied, the process proceeds to step S308.

In step S308, it is determined whether the reliability parameter of the left-eye image Conf0 is set to zero and the reliability parameter of the right-eye image Conf1 is set to one. If such a condition is satisfied, it can be determined that the result in the right-eye image outputted from the inter-frame mask detection result comparison unit 223-2 is more reliable than the result in the left-eye image outputted from the inter-frame mask detection result comparison unit 223-1.

In step S308, if it is determined that he reliability parameter of the left-eye image Conf0 is set to zero and the reliability parameter of the right-eye image Conf1 is set to one, the process proceeds to step S309.

In step S309, as a mask shape after correction for the right-eye image from the inter-stereo mask detection result comparison and correction unit 213, the result (X1'$_t$, Y1'$_t$, R1'$_t$) outputted from the inter-frame mask detection result comparison unit 223-2 is outputted without any modification.

On the other hand, parameters of the mask shape after correction in the left-eye image are calculated based on the following Equations (30) to (32).

$$X0'_t = X1'_t + D_{01} \tag{30}$$

$$Y0'_t = Y1'_t \tag{31}$$

$$R0'_t = R1'_t \tag{32}$$

In Equation (30), $D_{01}$ represents the distance between the centers of the mask for the left- and right-eye images, as shown in the following Equation (33).

$$D_{01} = X0 - X1 \tag{33}$$

In Equation (33), X0 represents x-coordinate of the center point of the mask shape for the left-eye image at a given time, and X1 represents x-coordinate of the center point of the mask shape for the right-eye image at a given time. For example, X0 and X1 may be previously determined, or they may be calculated when the reliability parameter for the left-eye image Conf0 of the inter-frame mask detection result comparison unit 223-1 and the reliability parameter for the right-eye image Conf1 of the inter-frame mask detection result comparison unit 223-2 are all set to one.

The parameters of the mask shape after correction in the left-eye image calculated in step S309 and the result outputted from the inter-frame mask detection result comparison unit 223-2 that is set as the mask shape after correction for the right-eye image are outputted to the subsequent processing unit, in step S305.

On the other hand, in step S308, if a condition that the reliability parameter of the left-eye image Conf0 is set to zero and the reliability parameter of the right-eye image Conf1 is set to one is determined not to be satisfied, the process proceeds to step S310.

The process proceeds to step S310 when the reliability parameter of the mask detection result in the left-eye image Conf0 is set to zero and the reliability parameter of the mask detection result in the right-eye image Conf1 is set to zero. In such a case, it can be determined that the mask detection result in the left-eye image and the mask detection result in the right-eye image have low reliability.

Alternatively, the process proceeds to step S310 when the reliability parameter of the mask detection result in the left-eye image Conf0 is set to one and the reliability parameter of the mask detection result in the right-eye image Conf1 is set to one. In such a case, it can be determined that the mask detection result in the left-eye image and the mask detection result in the right-eye image have high reliability.

When both of the mask detection result in the left-eye image and the mask detection result in the right-eye image have high reliability or low reliability, it is difficult to determine which of the mask detection results in the left-eye image and in the right-eye image is more reliable and which of them is proper to be used for correction.

In such a case, in step S310, based on the mask detection result in the image that is previously set among ones outputted from the inter-frame mask detection result comparison unit 223, the mask shape of the other image is corrected.

For example, if a mask detection result in the left-eye image is set to be processed, the inter-stereo mask detection result comparison and correction unit 213 outputs, as the mask shape after correction for the left-eye image, the result (X0'$_t$, Y0'$_t$, R0'$_t$) outputted from the inter-frame mask detection result comparison unit 223-1 without any modification, and outputs, as the mask shape after correction for the right-eye image, the parameter calculated based on Equations (26) to (28).

Which of the left-eye image and the right-eye image is to be processed may be determined previously, or processing of checking a change in the reliability parameters Conf0 and Conf1 and switching dynamically into one having higher reliability may be performed.

The parameter that is set in this way is outputted to the subsequent processing unit as the mask shape information (X0'$_t$, Y0'$_t$, R0'$_t$) of the left-eye image and mask shape information (X1'$_t$, Y1'$_t$, R1'$_t$) of the right-eye image after correction at time t in step S305 as described above, and then the processing in the inter-stereo mask detection result comparison and correction unit 213 is ended.

Furthermore, the mask shape information of the left-eye image after final correction at time t (X0'$_t$, Y0'$_t$, R0'$_t$) is stored in the mask detection result buffer 222-1, and the mask shape information of the right-eye image after final correction at time t (X1'$_t$, Y1'$_t$, R1'$_t$) is stored in the mask detection result buffer 222-2, and each information is used for the next frame.

Such processing will be described in detail with reference to FIG. 10.

Figure 10:
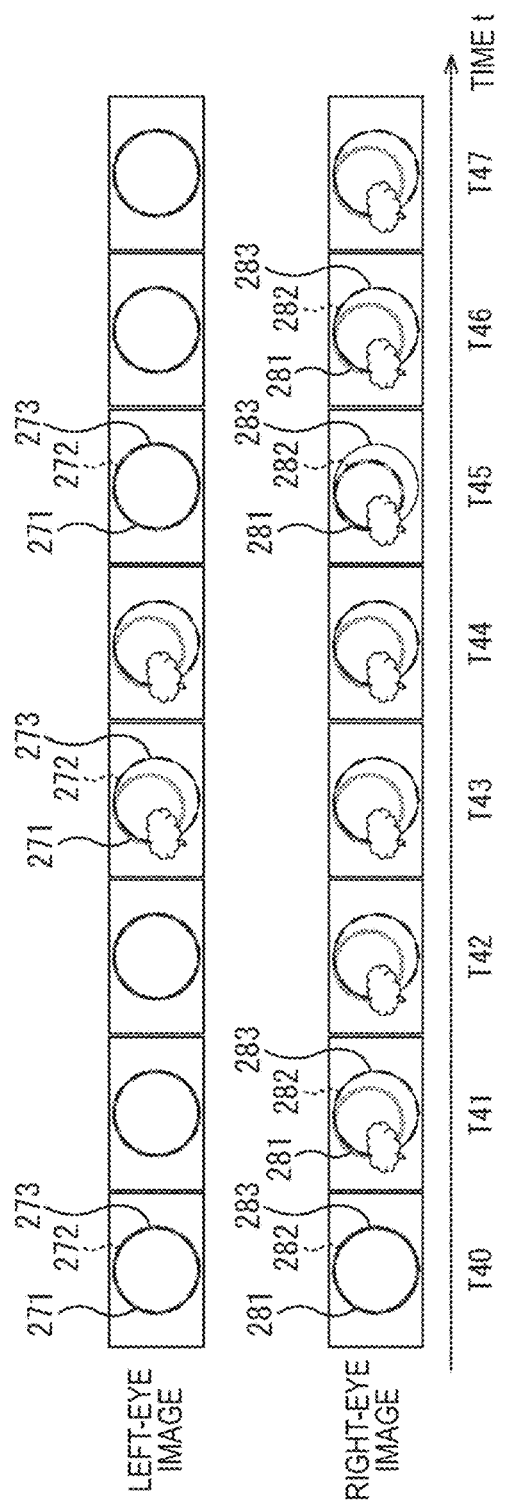
FIG. 10 is a diagram illustrated to describe the correction of a mask shape.

In FIG. 10, the horizontal axis t represents time and, images (frames) of the figures are images obtained in the past in the order of time toward the left side. In addition, the upper part in the figure represents a left-eye image to be processed or has been processed by the mask detection and correction unit 212-1 (see FIG. 6), and the lower part in the figure represents a right-eye image to be processed or has been processed by the mask detection and correction unit 212-2 (see FIG. 6). In FIG. 10, the mask region 252 is shown without being blackened.

In the figure, the thick solid-line circles 271 and 281 represent the result (mask detection result before correction) outputted from the mask detection unit 221 (see FIG. 6). The thin solid-line circles 272 and 282 in the figure represent the result (mask detection result after correction between frames) outputted from the inter-frame mask detection result comparison unit 223. The dotted-line circles 273 and 283 in the figure represent the result (mask detection result after final correction) outputted from the inter-stereo mask detection result comparison and correction unit 213.

A cloud-shaped mark in the figure represents a case in which the image is in a deteriorated condition for some reasons such as adhesion of dust or dirt on the lens included in an endoscopic device and then normal mask detection is not allowed to be performed. In the example shown in FIG. 10, such a situation is occurred in the frames at time T43 and time T44 in the left-eye image, and is occurred in the frames at time T41 to T47 in the right-eye image.

The following description will be given on the assumption that the threshold TH_CNT of the count value Cnt of the inter-frame mask detection result comparison unit 223 is set to five.

At time T41, in the right-eye image, the result (circle 281) outputted form the mask detection unit 221-2 is erroneous, but it is corrected by the inter-frame mask detection result comparison unit 223-2, which performs the right-eye image, using the result (circle 283) outputted from the inter-stereo mask detection result comparison and correction unit 213 at time T40. Thus, the absolute value of the difference between frames in the left- and right-eye images in the inter-stereo mask detection result comparison and correction unit 213 is within the range of threshold values.

At time T42, processing similar to that performed at time T41 is performed.

At time T43, in both the left-eye and right-eye images, the results (circles 271 and 281) outputted form the mask detection unit 221 are erroneous, but the results are corrected (circles 272 and 282) by the inter-frame mask detection result comparison units 223-1 and 223-2, respectively.

At time T44, processing similar to that performed at time T43 is performed.

At time T45, in the right-eye image, an erroneous mask detection of the mask detection unit 221-2 is continued, and thus the count value Cnt of the inter-frame mask detection result comparison unit 223-2 satisfies the threshold TH_CNT (=5). The result (circle 282) outputted from the inter-frame mask detection result comparison unit 223-2 is corrected to be the same as the result (circle 281) outputted from the mask detection unit 221-2.

At time T45, the reliability parameter Conf1 in the inter-frame mask detection result comparison unit 223-2 in the right-eye image is set to zero.

On the other hands, the detection result in the left-eye image at time T45 is correct. In the inter-frame mask detection result comparison unit 223-1, the absolute value of the difference with the result (circle 273) outputted from the inter-stereo mask detection result comparison and correction unit 213 at time T44 is within the threshold, and thus the reliability parameter Conf0 is set to one.

In the inter-stereo mask detection result comparison and correction unit 213, the absolute value of the difference of the results outputted from the respective inter-frame mask detection result comparison units 223 for the left-eye image and the right-eye image falls outside the threshold, and the mask shape for the right-eye image is corrected based on the result (circle 272) outputted from the inter-frame mask detection result comparison unit 223-1 for the left-eye image by the comparison of the reliability (Conf0=1 and Conf1=0). This correction is performed based on Equations (26) to (28).

In this way, both of the inter-frame mask detection result comparison unit 223 and the inter-stereo mask detection result comparison and correction unit 213 perform correction, and thus more stable detection of a mask is possible.

<When Operation is Started>

The mask detection and correction unit 112 of the image processing device 100 according to the first embodiment or the mask detection and correction unit 212 of the image processing device 200 according to the second embodiment may be configured to perform their respective operations in a normal condition or when a predetermine event occurs.

In the examples described above, the case in which the operation is performed in a normal condition, that is, for every frame has been described as an example. The following description will be given by exemplifying the image processing device 100 according to the first embodiment. When the operation is performed in a normal condition, the mask shape detected by the mask detection unit 121 is stored in the mask detection result buffer 122 for every frame, is corrected by the inter-frame mask detection result comparison unit 123, and is outputted as the mask shape after correction.

If the operation is performed when a predetermined event occurs, the parameter regarding the mask shape detected by the mask detection unit 121 for every frame is stored in the mask detection result buffer 122, and thus even when an event occurs at any timing, it is possible to deal with the event.

When a predetermined event occurs, correction by the inter-frame mask detection result comparison unit 123 is started using the parameter stored in the mask detection result buffer 122. Such configuration may be applied to the second embodiment.

The predetermined event includes an event when it is determined that an error occurs. Whether an error occurs can be determined, for example, using an average luminance level of the in-vivo region (effective region 151) in the image from the endoscopic device.

As an example, when the average luminance level is low, it is difficult to define the boundary between the mask region 152 and the in-vivo region (effective region 151), and thus detection of a mask is difficult to perform. In such a case, in other words, when the average luminance level is less than a predetermined threshold, the correction described above may be started on the assumption that an error occurs (occurrence of event).

Moreover, as another example of the predetermined event, the determination as to whether a rigid lens is inserted into a trocar is possible, and the event can be regarded as when the rigid lens is inserted into the trocar or the inserted rigid lens is released. In such a configuration, for example, the determination as to whether the rigid lens is inserted into the trocar is possible using a sensor attached to the trocar.

A mask shape obtained immediately before the rigid lens is removed may be stored, and the stored mask shape may be used until the rigid lens is inserted again.

Furthermore, as another example of the predetermined event, the mask shape may be corrected by considering, as an event, a mechanism for allowing the user to instruct correction of a mask, for example, for providing a button for such instruction and operating the button. For example, it is possible to correct the mask shape by considering, as an event, a mechanism for providing a foot switch and operating the foot switch.

It is possible to configure so that the mask shape may be corrected using such an external input.

<Recording Medium>

The series of processes described above can be executed by hardware but can also be executed by software. When the series of processes is executed by software, a program that constructs such software is installed into a computer. Here, the expression "computer" includes a computer in which dedicated hardware is incorporated and a general-purpose personal computer or the like that is capable of executing various functions when various programs are installed.

Figure 11:
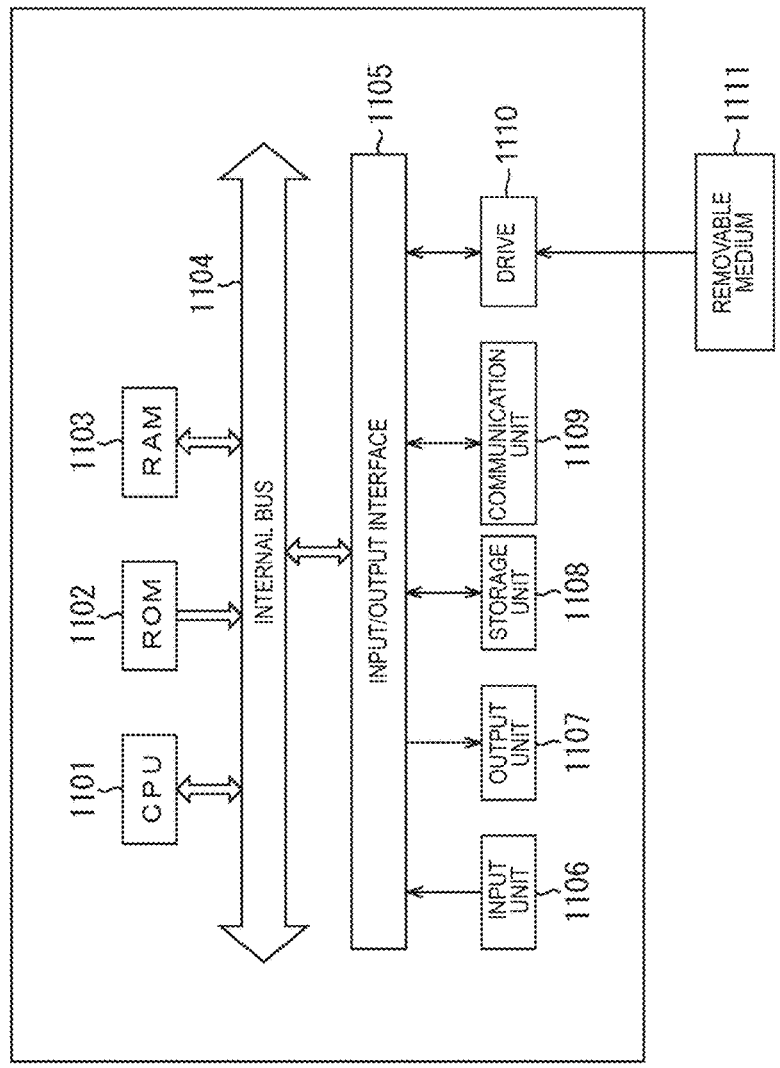
FIG. 11 is a diagram illustrated to describe a recording medium.

FIG. 11 is a block diagram illustrating a hardware configuration example of a computer for causing the above-described series of processes to be executed using a program. In the computer, a central processing unit (CPU) 1101, a read only memory (ROM) 1102, and a random access memory (RAM) 1103 are interconnected via a bus 1104. The bus 1104 is connected to an input/output interface 1105. The input/output interface 1105 is connected to an input unit 1106, an output unit 1107, a storage unit 1108, a communication unit 1109, and a drive 1110.

The input unit 1106 includes a keyboard, a mouse, a microphone, and other like devices. The output unit 1107 includes a display, a speaker, and other like devices. The storage unit 1108 includes a hard disk, a non-volatile memory, and other like devices. The communication unit 1109 includes a network interface and other like devices.

The drive 1110 drives a removable medium 1111 such as a magnetic disk, an optical disk, a magneto-optical disk, a semiconductor memory or the like.

In the computer configured as described above, as one example the CPU 1101 loads a program stored in the storage unit 1108 via the input/output interface 1105 and the bus 1104 into the RAM 1103 and executes the program to carry out the series of processes described earlier.

Programs to be executed by the computer (CPU 1101) are provided being recorded in the removable medium 1111 in the form of a packaged medium or the like. The programs may be provided via a wired or wireless transmission medium, such as a local area network, the Internet, or digital satellite broadcasting.

In the computer, by inserting the removable medium 1111 into the drive 1110, the program can be installed in the storage unit 1108 via the input/output interface 1105. Further, the communication unit 1109 can receive the program via a wired or wireless transmission medium and can install it in the storage unit 1108. Moreover, the program can be installed in advance in the ROM 1102 or the storage unit 1108.

It should be noted that the program executed by a computer may be a program that is processed in time series according to the sequence described herein or a program that is processed in parallel or at necessary timing such as upon calling.

Note that the term "system" used herein refers to an entire configuration composed of a plurality of devices.

Note that the advantages described herein are to be considered illustrative or exemplary rather than restrictive, and other advantages that will be understood from the present technology may be achievable.

An embodiment of the technology is not limited to the embodiments described above, and various changes and modifications may be made without departing from the scope of the technology.

Additionally, the present technology may also be configured as below.

(1) An image processing device including:
a detection unit configured to detect a mask from an acquired image;
a determination unit configured to determine whether there is a change in the mask detected by the detection unit; and
an output unit configured to output a parameter when the determination unit determines that there is a change in the mask, the parameter being related to the mask detected by the detection unit before it is determined that there is a change in the mask.

(2) The image processing device according to (1),
wherein the determination unit determines whether there is a change in the mask based on a temporal change in a parameter of the mask detected by the detection unit.

(3) The image processing device according to (2),
wherein the determination unit determines that there is no change in the mask detected by the detection unit when a difference between a parameter of a first mask detected by the detection unit and a parameter of a second mask detected by the detection unit after the first mask is detected is less than a predetermined threshold, and
wherein the output unit outputs a parameter of a third mask when the determination unit determines that there is no change in the mask, the parameter of the third mask being calculated from the parameter of the first mask and the parameter of the second mask.

(4) The image processing device according to (2),
wherein the determination unit determines that there is a change in the mask detected by the detection unit when a difference between a parameter of a first mask detected by the detection unit and a parameter of a second mask detected by the detection unit after the first mask is detected is greater than or equal to a predetermined threshold, and
wherein the output unit outputs the parameter of the first mask when the determination unit determines that there is a change in the mask.

(5) The image processing device according to (4),
wherein the output unit outputs the parameter of the second mask instead of the parameter of the first mask when the determination unit determines that there is a change in the mask by a predetermined number of times.

(6) The image processing device according to (4),
wherein the output unit outputs a parameter of a third mask calculated from the parameter of the first mask and the parameter of the second mask when the determination unit determines that there is a change in the mask by a predetermined number of times.

(7) The image processing device according to any one of (1) to (6),
wherein the acquired image is an image captured by an endoscope.

(8) The image processing device according to (1), further including:
a correction unit configured to correct a parameter of the mask using a reliability parameter representing reliability of a parameter of the mask.

(9) The image processing device according to (1),
wherein the detection unit detects a first mask and a second mask from two respective acquired images, and
wherein the image processing device further includes a correction unit configured to determine whether at least one of a parameter of the first mask and a parameter of the second mask is to be corrected, based on the parameter of the first mask and the parameter of the second mask.

(10) The image processing device according to (9),
wherein the correction unit corrects one of the parameter of the first mask and the parameter of the second mask using the other parameter that is set previously, when a difference between the parameter of the first mask and the parameter of the second mask is outside a predetermined range.

(11) The image processing device according to (9),
wherein the correction unit performs correction using a reliability parameter representing reliability of each of the parameter of the first mask and the parameter of the second mask when a difference between the parameter of the first mask and the parameter of the second mask is outside a predetermined range.

(12) The image processing device according to any one of (1) to (11),
wherein the determination unit determines whether there is a change in the mask based on a luminance level of the image.

(13) The image processing device according to (12),
wherein the determination unit determines that there is a change in the mask when an average luminance level of the image is less than a predetermined threshold.

(14) The image processing device according to any one of (1) to (13),
wherein the determination unit determines whether there is a change in the mask based on whether an endoscope is inserted into a trocar.

(15) The image processing device according to (14),
wherein the determination unit determines that there is a change in the mask when it is determined that an endoscope is not inserted into a trocar.
(16) The image processing device according to any one of (1) to (15),
wherein the determination unit determines whether there is a change in the mask based on an external input.
(17) The image processing device according to (16),
wherein the external input is provided using a foot switch.
(18) An image processing method including:
detecting a mask from an acquired image;
determining whether there is a change in the detected mask; and
outputting a parameter when it is determined that there is a change in the mask, the parameter being related to the mask detected before it is determined that there is a change in the mask.

What is claimed is:

1. A medical image processing device comprising:
   circuitry configured to:
   detect a mask from image data obtained by a medical imaging device, the mask is defined by a region in an in-vivo image that is blocked by mechanical vignetting;
   determine whether there is a temporal change of the detected mask, based on a first mask detected at a first point of time and a second mask with a different detectable region from the first mask detected at a second point of time, the first point of time being before the second point of time; and
   output information regarding the first mask in a case the circuitry determines that there is a temporal change of the detected mask for generating display information for display.

2. The medical image processing device according to claim 1,
   wherein the circuitry determines that there is the temporal change of the mask when a difference between the first mask and the second mask is greater than or equal to a predetermined threshold.

3. The medical image processing device according to claim 2,
   wherein the circuitry outputs second mask instead of the first mask in a case the circuitry determines that there is a temporal change of the mask by a predetermined number of times.

4. The medical image processing device according to claim 2,
   wherein the circuitry outputs a corrected mask obtained from the second mask and the first mask instead of the first mask in a case the circuitry determines that there is a temporal change of the mask by a predetermined number of times.

5. The medical image processing device according to claim 1, wherein
   the circuitry determines that there is no temporal change of the mask in a case a difference between the first mask and the second mask is less than a predetermined threshold, and
   the circuitry outputs a corrected mask in a case the circuitry determines that there is no temporal change of the mask, the corrected mask being obtained from the second mask and the first mask.

6. The medical image processing device according to claim 1,
   wherein the medical imaging device comprises an endoscope.

7. The medical image processing device according to claim 1,
   wherein the mask represents non-effective region.

8. The medical image processing device according to claim 1,
   wherein the circuitry is configured to correct the second mask using a reliability parameter representing reliability of the second mask.

9. The medical image processing device according to claim 1,
   wherein the circuitry is configured to determine whether there is a temporal change of the mask based on a luminance level of the image data.

10. The medical image processing device according to claim 9,
    wherein the circuitry determines that there is a temporal change of the mask in a case an average luminance level of the image data is less than a predetermined threshold.

11. The medical image processing device according to claim 1,
    wherein the circuitry determines that there is a temporal change of the mask in a case an endoscope is not inserted into a trocar.

12. The medical image processing device according to claim 1,
    wherein the circuitry is configured to determine whether there is a temporal change of the mask based on an external input.

13. The medical image processing device according to claim 12,
    wherein the external input is received from a foot switch.

14. The medical image processing device according to claim 1, wherein
    the circuitry detects first mask information and second mask information from two respective images, and
    the circuitry determines whether at least one of the first mask information and the second mask information is to be corrected, based on the first mask information and the second mask information.

15. The medical image processing device according to claim 14,
    wherein the medical imaging device comprises a stereo endoscope.

16. The medical image processing device according to claim 14,
    wherein the circuitry corrects one of the first mask information and the second mask information, in a case a difference between the first mask information and the second mask information is outside a predetermined range.

17. The medical image processing device according to claim 14,
    wherein the circuitry performs correction using a reliability parameter representing reliability of each of the first mask information and the second mask information in a case a difference between the first mask information and the second mask information is outside a predetermined range.

18. The medical image processing device according to claim 1, wherein the second point of time is a current time.

19. A medical image processing method comprising:
    detecting, with circuitry, a mask from image data obtained by a medical imaging device, the mask is defined by a region in an in-vivo image that is blocked by mechanical vignetting;

determining whether there is a temporal change of the detected mask, based on a first mask detected at a first point of time and a second mask with a different detectable region from the first mask detected at a second point of time, the first point of time being before the second point of time; and outputting information regarding the first mask in a case the circuitry determines that there is a temporal change of the detected mask for generating display information for display.

20. A medical imaging system comprising:

a medical imaging device configured to output image data; and circuitry configured to detect a mask from image data obtained by a medical imaging device, the mask is defined by a region in an in-vivo image that is blocked by mechanical vignetting;

determine whether there is a temporal change of the detected mask, based on a first mask detected at a first point of time and a second mask with a different detectable region from the first mask detected at a second point of time, the first point of time being before the second point of time; and output information regarding the first mask in a case the circuitry determines that there is a temporal change of the detected mask for generating display information for display.

21. The medical imaging system according to claim 20, wherein the medical imaging device comprises an endoscope.

22. A non-transitory computer readable medium including executable instructions, which when executed by a computer cause the computer to execute a medical image processing method, the method comprising:

detecting a mask from image data obtained by a medical imaging device, the mask is defined by a region in an in-vivo image that is blocked by mechanical vignetting;

determining whether there is a temporal change of the detected mask, based on a first mask detected at a first point of time and a second mask with a different detectable region from the first mask detected at a second point of time, the first point of time being before the second point of time; and outputting information regarding the first mask in a case the circuitry determines that there is a temporal change of the detected mask for generating display information for display.

23. A medical image processing device comprising:

circuitry configured to:

detect a mask from image data obtained by a medical imaging device, the mask being a region in which an in-vivo image is blocked by mechanical vignetting;

determine whether there is a temporal change of the detected mask, based on a first mask detected at a first point of time and a second mask detected at a second point of time, the first point of time being before the second point of time; and output information regarding the first mask in a case the circuitry determines that there is a temporal change of the detected mask for generating display information for display, wherein the circuitry outputs a corrected mask obtained from both the second mask and the first mask instead of only the first mask in a case the circuitry determines that there is a temporal change of the mask a predetermined number of times.

* * * * *